(12) United States Patent
Schumann et al.

(10) Patent No.: US 7,763,154 B2
(45) Date of Patent: Jul. 27, 2010

(54) METHOD AND SENSOR ELEMENT FOR DETERMINING A GAS IN A GAS MIXTURE

(75) Inventors: Bernd Schumann, Rutesheim (DE); Thorsten Ochs, Schwieberdingen (DE)

(73) Assignee: Robert Bosch GmbH, Stuttgart (DE)

( * ) Notice: Subject to any disclaimer, the term of this patent is extended or adjusted under 35 U.S.C. 154(b) by 1208 days.

(21) Appl. No.: 10/932,741

(22) Filed: Sep. 2, 2004

(65) Prior Publication Data

US 2005/0077178 A1      Apr. 14, 2005

(30) Foreign Application Priority Data

Sep. 3, 2003    (EP) ................... 03019971

(51) Int. Cl.
*G01N 27/407* (2006.01)

(52) U.S. Cl. .................... 204/424; 204/425; 205/780.5; 205/787; 73/23.31

(58) Field of Classification Search .......... 204/402, 204/424, 425, 426, 427; 205/781, 783.5, 205/787, 780.5; 73/23.31
See application file for complete search history.

(56) References Cited

U.S. PATENT DOCUMENTS

| | | | |
|---|---|---|---|
| 5,879,525 A | * | 3/1999 | Kato .......................... 204/424 |
| 5,893,968 A | | 4/1999 | Kato |
| 7,153,402 B2 | * | 12/2006 | Nakagaki et al. ............ 204/425 |
| 2002/0011410 A1 | * | 1/2002 | Inoue et al. ................. 204/426 |
| 2002/0043461 A1 | * | 4/2002 | Stahl ........................ 204/425 |
| 2003/0121801 A1 | * | 7/2003 | Inaba et al. .............. 205/785.5 |

FOREIGN PATENT DOCUMENTS

| | | |
|---|---|---|
| DE | 198 51 949 | 10/2000 |
| DE | 100 230 62 | 11/2001 |
| DE | 100 58 014 | 12/2002 |
| EP | 678 740 | 10/1995 |
| JP | 2000-193639 | 7/2000 |
| WO | WO 02/065113 | 8/2002 |

\* cited by examiner

*Primary Examiner*—Kaj K Olsen
(74) *Attorney, Agent, or Firm*—Kenyon & Kenyon LLP

(57) ABSTRACT

A method and a sensor element are provided for determining the concentration of an oxidizable gas in a gas mixture, e.g., in exhaust gases of internal combustion engines. Within the sensor element of a gas sensor, nitrogen oxides, hydrogen, and/or carbon monoxide contained in the gas mixture are at least partially removed in an initial step. In a further step, the concentration of the gas to be detected in the gas mixture freed of nitrogen oxides, carbon monoxide and/or hydrogen is ascertained.

19 Claims, 1 Drawing Sheet

METHOD AND SENSOR ELEMENT FOR DETERMINING A GAS IN A GAS MIXTURE

FIELD OF THE INVENTION

The present invention relates to a method and a sensor element of a gas sensor for determining the concentration of a gas in a gas mixture.

BACKGROUND INFORMATION

In view of the more stringent environmental-pollution guidelines that are being implemented, the sensor system for detecting combustion engines' exhaust gases is becoming increasingly important. In this context, gas sensors based on solid electrolyte are often used, which identify the gaseous components to be detected in the exhaust gas in a highly selective manner. A special challenge in this context is the determination of concentrations, e.g., of oxidizable exhaust gas components, especially in cases where the relevant internal combustion engine is operated under oxygen-rich conditions. One example of this challenge is the identification of hydrocarbons or ammonia in exhaust gases of internal combustion engines that are operated with a surplus of oxygen.

Published European patent document EP 678 740 describes a gas sensor based on solid electrolyte, which is used to identify nitrogen oxides. The measuring principle of the sensor is based on removing excess oxygen within the gas sensor without changing the concentration of nitrogen oxide and, following the formation of a constant low oxygen atmosphere, amperometrically ascertaining the concentration of nitrogen oxides. This sensor can also be used, inter alia, for determining the concentration of hydrogen or ammonia. For this purpose, however, the sensor must feature a proton-conducting solid electrolyte layer, the installation of which layer is expensive and the durability of which layer is limited.

An object of the present invention is to provide a method and a sensor element for a gas sensor which reliably and cost-effectively provide the determination of a gas in a gas mixture.

SUMMARY OF THE INVENTION

The method and the sensor element according to the present invention enable measurements of oxidizable components of a gas mixture even in the presence of larger quantities of oxygen and nitrogen oxides. To this end, using an auxiliary electrode within the sensor element, a large part of the nitrogen oxides present is advantageously reduced and a large part of the hydrogen or carbon monoxide present is advantageously oxidized and removed from the gas mixture. In this manner, a more precise determination of the gas to be detected is made possible.

According to the method of the present invention, in a first step, oxygen contained in the gas mixture or nitrogen oxides contained in the gas mixture are reduced using a first auxiliary electrode of the sensor element and are at least partly removed from the gas mixture. In a second step, the concentration of the nitrogen oxides still present in the gas mixture is further reduced using an additional auxiliary electrode. In addition, hydrogen and/or carbon monoxide, which may form as a by-product of the reduction performed in the first step, are oxidized since these gases hamper the determination particularly of oxidizable gases. These steps allow for a particularly exact determination of the concentration of the gas to be measured.

In an example embodiment according to the present invention, the first auxiliary electrode has two parts, i.e., a first region made of a first material having a first catalytic activity and a second region made of a second material having a second catalytic activity. This arrangement allows for the use of strongly negative potentials at the first auxiliary electrode, and hence allows for a high pumping capacity of this electrode per unit surface area without a loss of selectivity for the gases to be removed.

DETAILED DESCRIPTION

Figure 1:
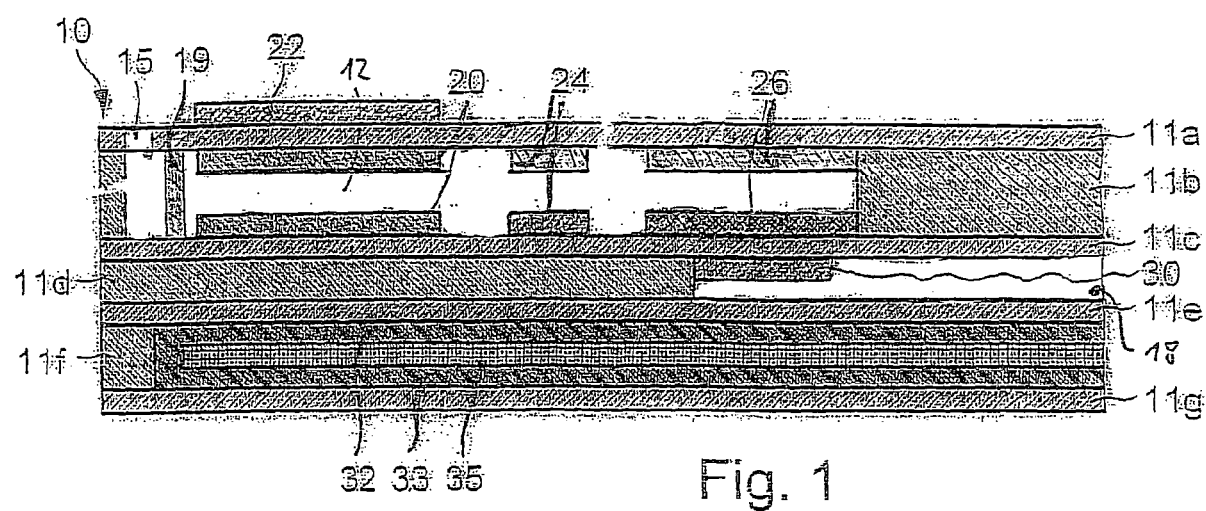
FIG. 1 shows a cross-sectional view of a section of an example embodiment of the sensor element according to the present invention which is facing the gas to be measured.

FIG. 1 shows a basic construction of a first example embodiment of the sensor element according to the present invention. Reference numeral 10 denotes a planar sensor element of an electrochemical gas sensor used for determining a gas in a gas mixture, e.g., the concentration of an oxidizable gas such as ammonia, a hydrocarbon, hydrogen sulfide, sulfur monoxide or an alkyl amine in the exhaust gases of internal combustion engines. The sensor element features a plurality of oxygen-ion-conducting solid electrolyte layers 11a, 11b, 11c, 11d, 11e, 11f and 11g, which are designed, for example, as ceramic foils and which form a planar ceramic body. More particularly, the oxygen-ion-conducting solid electrolyte layers 11a-11g may be made of materials such as $Y_2O_3$-stabilized or partially stabilized $ZrO_2$, for example. Alternatively, solid electrolyte layers 11a-11g may be substituted with foils made of aluminum oxide, at least in places where ionic conduction in the solid electrolyte is unimportant or undesired.

The integrated form of the planar ceramic body of sensor element 10 is produced by initially laminating together the ceramic foils printed with functional layers, and by subsequently sintering the laminated structure.

Sensor element 10 contains, for example, an inner gas compartment 12 and a reference gas channel 18. Via a gas intake, which at one end leads out of the planar body of sensor element 10, reference gas channel 18 is in contact with a reference gas, which may be the surrounding air, for example.

Inner gas compartment 12 has an opening 15, which allows for contact with the gas mixture to be analyzed. Opening 15 is arranged in the solid electrolyte layer 11a, perpendicularly to the top surface of sensor element 10, but the opening 15 may also be formed in solid electrolyte layer 11b.

At least one first auxiliary electrode 20 (e.g., a pair of electrodes 20) is provided in inner gas compartment 12. At least one additional auxiliary electrode 24 (e.g., a pair of electrodes 24) is situated downstream in the direction of the diffusion of the gas mixture. On the outer side of solid electrolyte layer 11a, which directly faces the gas to be measured, there is an outer electrode 22, which may be covered by a porous protective layer (not shown).

Together with the outer electrode 22, auxiliary electrodes 20, 24 form electrochemical pumping cells. With the aid of the pumping cells, a constant oxygen partial pressure is set in the inner gas compartment 12. For monitoring the set oxygen partial pressure, at least one of the auxiliary electrodes 20, 24 is additionally interconnected with a reference electrode 30, situated in reference gas channel 18, to form a so-called Nernst or concentration cell. This allows the oxygen potential of auxiliary electrodes 20, 24, which is a function of the oxygen concentration in the inner gas compartment 12, to be directly compared to the constant oxygen potential of reference electrode 30 in the form of a measurable electrical voltage. The magnitude of the pumping voltages to be applied to the pumping cells is chosen in such a way that a constant voltage is formed between electrodes 20 and 30 (or between 24 and 30) of the concentration cells.

Furthermore, the potential applied at the first auxiliary electrodes 20 is chosen in such a way that gases such as nitrogen or sulfur oxides which may be contained in the gas mixture are likewise reduced and thus removed from the gas mixture. This reduces the danger of a reaction within the sensor element between the target gas to be detected and gases that have an oxidizing effect.

In the direction of the diffusion of the gas mixture, downstream of auxiliary electrodes 20, 24, inner gas compartment 12 additionally features at least one measuring electrode 26 (e.g., a pair of measuring electrodes 26), which in conjunction with reference electrode 30 or outer electrode 22 forms an additional pumping cell. This pumping cell 26, 30 or 26, 22 is used to identify the gas to be determined (the target gas to be detected), the gas to be determined being specifically oxidized or reduced at the surface of measuring electrode 26 and oxygen being electrochemically pumped in or pumped off for this purpose. The pumping current flowing between the measuring electrode 26 and the reference electrode 30, or flowing between the measuring electrode 26 and the outer electrode 22, is used as a gauge for the concentration of the gas to be determined.

To ensure that the gas to be determined is not decomposed at first auxiliary electrodes 20, first auxiliary electrodes 20 are made of a catalytically inactive material. This can be, for example, platinum or a platinum alloy, e.g., a gold-platinum alloy having a gold content of up to 2 wt %. The potential at the first auxiliary electrode may lie between −200 and −900 mV, e.g., between −400 and −700 mV.

In another example embodiment of the present invention, the auxiliary electrode is divided into two electrically connected regions, which differ with respect to the electrode material on which they are based, and hence also differ with respect to their catalytic activity. Thus, for example, a first region of auxiliary electrode 20 may be made of a platinum-precious metal alloy, e.g., a platinum-gold alloy, and a second region may be made of platinum. The first region may be located in front of the second region in the direction of flow of the gas mixture, so that the gas mixture first meets the catalytically less active first region of auxiliary electrode 20 before contacting the catalytically more active second region. It is also possible, however, to reverse the order of the first and second regions. A region in the sense of the present application is defined as a contiguous area representing a significant percentage of the total surface area.

The additional auxiliary electrode 24 may be made of the same material as first auxiliary electrode 20, i.e., made of platinum or a platinum alloy, e.g., a gold-platinum alloy. At the additional auxiliary electrode 24, the oxygen or sulfur oxide or nitrogen oxide concentration of the gas mixture is further reduced with respect to the level already established at the first auxiliary electrode 20. Furthermore, the potential set at the additional auxiliary electrode allows for hydrogen contained in the gas mixture to be oxidized into water, or for carbon monoxide contained in the gas mixture to be oxidized into carbon dioxide. Hydrogen or carbon monoxide may either be already contained in the gas mixture to be measured, or it may be formed at first auxiliary electrode 20 by the strong negative potential present there. The removal of the hydrogen or carbon monoxide at the additional auxiliary electrode 24 allows for a more precise determination of oxidizable gases in the gas mixture since the measurement is not distorted by fluctuating hydrogen or carbon monoxide contents in the gas mixture. To this end, a potential of −350 to −500 mV is applied at the additional auxiliary electrode 24.

The measuring electrode 26, by contrast, is designed to be catalytically active and is made of, for example, rhodium, a platinum-rhodium alloy or another suitable platinum alloy. The outer electrode 22 as well as the reference electrode 30 are likewise made of a catalytically active material such as platinum, for example. In this context, the electrode material for all the electrodes may be applied as cermet in order to sinter the electrode material to the ceramic foils.

Additionally, a resistance heater 35 is embedded in the ceramic base of sensor element 10 between two electrical insulating layers 32, 33. Resistance heater 35 is used to heat sensor element 10 up to the required operating temperature of 600 to 900° C., for example.

Within the inner gas compartment 12, a porous diffusion barrier 19 is situated in front of the first auxiliary electrodes 20 in the direction of diffusion of the gas mixture. Porous diffusion barrier 19 constitutes a diffusion resistor with regard to the gas mixture diffusing towards the first auxiliary electrodes 20. Additionally, a further porous diffusion barrier may be provided in the inner gas compartment 12 between the first auxiliary electrode 20 and the additional auxiliary electrode 24 in order to achieve the formation of different oxygen concentrations in different regions of the inner gas compartment 12.

The potential at the first auxiliary electrode 20 as well as the potential at the additional auxiliary electrode 24 may be selected in such a way that there is no significant decomposition of the gas to be determined at either of the two electrodes.

As an alternative to an amperometric determination of the gas to be measured using pumping cell 26, 30, a potentiometric determination may be performed as well.

To this end, measuring electrode 26 is designed to be catalytically inactive through the use of suitable platinum, silver and palladium alloys so that a disequilibrium potential is formed at its surface, the magnitude of which is a direct function of the concentration of the gas to be measured. This operating method is suitable for determining oxidizable gases.

The potential formed at the measuring electrode 26 may be determined as a measurable voltage with respect to the constant potential of reference electrode 30.

A further example embodiment for detecting the target gas to be measured makes use of a resistive measuring element. For this purpose, an additional electrode (not shown) may be situated in the inner gas compartment 12, which is in contact with the measuring electrode 26 via a layer sensitive to the target gas to be measured. A voltage is applied to the measuring electrode 26 and to the additional electrode, and the resistance of the gas-sensitive layer between the two electrodes is determined.

What is claimed is:

1. A sensor element for determining the concentration of a target gas in a gas mixture, comprising:
   at least one first auxiliary electrode in direct contact with the gas mixture;
   at least one second auxiliary electrode in direct contact with the gas mixture, the at least one second auxiliary electrode configured to at least partially remove nitrogen oxide contained in the gas mixture, the second auxiliary electrode having a first surface region containing a platinum-precious metal alloy and a separate second surface region containing platinum, the second surface region being catalytically more active than the first surface region and disposed downstream from the first surface region with respect to a flow of the gas mixture, so that the gas mixture contacts the first region before contacting the second region; and a measuring electrode in direct contact with the gas mixture, the measuring electrode arranged to measure the gas mixture after the gas mixture has diffused downstream from the at least one second auxiliary electrode;

wherein the at least one first auxiliary electrode is at least temporarily connected to a potential such that at least one of hydrogen, carbon monoxide and nitrogen oxide contained in the gas mixture is at least partially removed from the sensor element, and wherein a signal generated using the measuring electrode is used to determine the concentration of the target gas.

2. The sensor element as recited in claim 1, wherein the potential is between −350 mV to −500 mV.

3. The sensor element as recited in claim 1, wherein a potential between −350 mV to −500 mV is applied to the first auxiliary electrode for at least one of oxidizing at least one of hydrogen and carbon monoxide contained in the gas mixture and reducing the amount of nitrogen oxide contained in the gas mixture, and wherein a potential between −400 mV to −700 mV is applied to the second auxiliary electrode for reducing the amount of at least one of oxygen and nitrogen oxide contained in the gas mixture.

4. The sensor element as recited in claim 1, wherein the target gas includes at least one of ammonia and a hydrocarbon.

5. The emission control system of claim 1, wherein the platinum-precious metal alloy is a platinum-gold alloy.

6. An emission control system for an internal combustion engine, comprising:
a sensor element for determining the concentration of a target gas in a gas mixture, the sensor element including:
at least one first auxiliary electrode in direct contact with the gas mixture;
at least one second auxiliary electrode in direct contact with the gas mixture, the at least one second auxiliary electrode configured to at least partially remove nitrogen oxide contained in the gas mixture, the second auxiliary electrode having a first surface region containing a platinum-precious metal alloy and a separate second surface region containing platinum, the second surface region being catalytically more active than the first surface region and disposed downstream from the first surface region with respect to a flow of the gas mixture so that the gas mixture contacts the first region before contacting the second region; and
a measuring electrode in direct contact with the gas mixture, the measuring electrode arranged to measure the gas mixture after the gas mixture has diffused downstream from the at least one second auxiliary electrode;
wherein the at least one first auxiliary electrode is at least temporarily connected to a potential such that at least one of hydrogen, carbon monoxide and nitrogen oxide contained in the gas mixture is at least partially removed from the sensor element, and wherein a signal generated using the measuring electrode is used to determine the concentration of the target gas.

7. The emission control system of claim 6, wherein the platinum-precious metal alloy is a platinum-gold alloy.

8. A sensor element for determining characteristics of a gas in a gas mixture, comprising:

electrochemical cells that each contains a respective electrode and a respective counter-electrode, wherein:
each of a first auxiliary electrode, an additional auxiliary electrode, and a measuring electrode is in direct contact with the gas mixture and is provided as one of the respective electrodes of the electrochemical cells, the measuring electrode positioned downstream from the additional auxiliary electrode;
a signal generated via the measuring electrode is used to determine a concentration of the gas;
the first auxiliary electrode has a first surface region and a second surface region electroconductively connected to each other, the second surface region being catalytically more active than the first surface region and disposed downstream from the first surface region with respect to a flow of the gas mixture so that the gas mixture contacts the first region before contacting the second region; and
the additional auxiliary electrode is arranged for application of a potential thereto such that:
(a) at least one of hydrogen and carbon monoxide contained in the gas mixture is at least partially removed via oxidization; and
(b) nitrogen oxides contained in the gas mixture are removed via reduction.

9. The sensor element of claim 8, wherein the gas mixture, the characteristics of the gas in which the sensor element is configured to determine, is of exhaust gases of an internal combustion engine.

10. The sensor element of claim 8, wherein the gas, the characteristics of which the sensor element is configured to determine, is an oxidizable gas.

11. The sensor element of claim 10, wherein:
the measuring electrode is arranged for oxidizing the oxidizable gas, during which oxidization a pumping current flows; and
the pumping current is the signal used to determine the concentration.

12. The sensor element of claim 8, wherein the sensor element is configured for:
values of a concentration of oxygen contained in the gas mixture and a concentration of the nitrogen oxide contained in the gas mixture to be set within the sensor element to initial values using the first auxiliary electrode; and
the concentration of the gas to be determined after the removal of the at least one of hydrogen, carbon monoxide, and nitrogen oxides from the gas mixture.

13. The sensor element of claim 8, wherein the potential is of −350 mV and of −500 mV.

14. The sensor element of claim 8, wherein:
a potential of −400 mV to −700 mV is applied to the first auxiliary electrode for reducing oxygen and nitrogen oxides contained in the gas mixture; and
a potential of −350 mV to −500 mV is applied to the additional auxiliary electrode.

15. The sensor element of claim 8, wherein the gas, the characteristics of which the sensor element is configured to determine, is at least one of ammonia and a hydrocarbon.

16. The emission control system of claim 8, wherein the platinum-precious metal alloy is a platinum-gold alloy.

17. An emission control system for an internal combustion engine, comprising:
a sensor element for determining characteristics of a gas in a gas mixture, the sensor element including:

electrochemical cells that each contains a respective electrode and a respective counter-electrode, wherein:

each of a first auxiliary electrode, an additional auxiliary electrode, and a measuring electrode is in direct contact with the gas mixture and is provided as one of the respective electrodes of the electrochemical cells, the measuring electrode positioned downstream from the additional auxiliary electrode;

a signal generated via the measuring electrode is used to determine a concentration of the gas;

the first auxiliary electrode has a first surface region and a second surface region electroconductively connected to each other, the second surface region being catalytically more active than the first surface region and disposed downstream from first surface region with respect to a flow of the gas mixture so that the gas mixture contacts the first region before contacting the second region; and the additional auxiliary electrode is arranged for application of a potential thereto such that:

(a) at least one of hydrogen and carbon monoxide contained in the gas mixture is at least partially removed via oxidization; and (b) nitrogen oxides contained in the gas mixture are removed via reduction.

18. The emission control system of claim 17, wherein the platinum-precious metal alloy is a platinum-gold alloy.

19. A sensor element for determining the concentration of a target gas in a gas mixture, comprising:

at least one first auxiliary electrode in direct contact with the gas mixture;

at least one second auxiliary electrode in direct contact with the gas mixture, the at least one second auxiliary electrode configured to at least partially remove nitrogen oxide contained in the gas mixture, the second auxiliary electrode having a first surface region containing a platinum-gold alloy and a separate second surface region containing platinum, the second surface region being catalytically more active than the first surface region and disposed downstream from the first surface region with respect to a flow of the gas mixture; and a measuring electrode in direct contact with the gas mixture, the measuring electrode arranged to measure the gas mixture after the gas mixture has diffused downstream from the at least one second auxiliary electrode;

wherein the at least one first auxiliary electrode is at least temporarily connected to a potential such that at least one of hydrogen, carbon monoxide and nitrogen oxide contained in the gas mixture is at least partially removed from the sensor element, and wherein a signal generated using the measuring electrode is used to determine the concentration of the target gas.

* * * * *